(12) United States Patent
Greager et al.

(10) Patent No.: US 10,065,911 B2
(45) Date of Patent: Sep. 4, 2018

(54) PROCESS OF REMOVING HEAT

(71) Applicant: Velocys, Inc., Plain City, OH (US)

(72) Inventors: Ivan Phillip Greager, Katy, TX (US); Steven Claude LeViness, Houston, TX (US); Roger Allen Harris, Dublin, OH (US); Andre Peter Steynberg, Dublin, OH (US); Jasmeer Jaichland Ramlal, Katy, TX (US); Dennis Parker, Houston, TX (US); John Dolan, Tulsa, OK (US)

(73) Assignee: Velocys Technologies Ltd., Abingdon, Oxfordshire (GB)

( * ) Notice: Subject to any disclaimer, the term of this patent is extended or adjusted under 35 U.S.C. 154(b) by 0 days.

(21) Appl. No.: 15/817,308

(22) Filed: Nov. 20, 2017

(65) Prior Publication Data

US 2018/0072643 A1   Mar. 15, 2018

Related U.S. Application Data

(62) Division of application No. 14/918,314, filed on Oct. 20, 2015, now Pat. No. 9,822,049.

(60) Provisional application No. 62/066,233, filed on Oct. 20, 2014.

(51) Int. Cl.
| | | |
|---|---|---|
| *C10G 2/00* | (2006.01) | |
| *B01J 19/00* | (2006.01) | |
| *C07C 29/151* | (2006.01) | |
| *B01J 8/00* | (2006.01) | |

(52) U.S. Cl.
CPC .......... *C07C 29/1512* (2013.01); *B01J 8/001* (2013.01); *B01J 19/0013* (2013.01); *C10G 2/32* (2013.01); *C10G 2/34* (2013.01); *B01J 2208/00106* (2013.01); *B01J 2208/00539* (2013.01); *B01J 2208/00548* (2013.01); *B01J 2208/00628* (2013.01); *B01J 2208/00637* (2013.01); *B01J 2219/0002* (2013.01); *B01J 2219/0004* (2013.01); *B01J 2219/00038* (2013.01); *B01J 2219/00074* (2013.01); *B01J 2219/00162* (2013.01); *B01J 2219/00164* (2013.01); *B01J 2219/00186* (2013.01); *Y02P 20/582* (2015.11)

(58) Field of Classification Search
CPC ..... C10G 2/00; C10G 2/32; C10G 3/60; B01J 19/0013
See application file for complete search history.

(56) References Cited

U.S. PATENT DOCUMENTS

| | | |
|---|---|---|
| 6,106,695 A | 8/2000 | Kalnes et al. |
| 7,294,734 B2 | 11/2007 | Brophy et al. |
| 7,468,455 B2 | 12/2008 | Mazanec et al. |
| 7,745,667 B2 | 6/2010 | Deshmukh et al. |
| 8,703,984 B2 | 4/2014 | Mazanec et al. |

(Continued)

OTHER PUBLICATIONS

International Search Report from International Application No. PCT/GB2015/053131, dated Jan. 23, 2017.

(Continued)

*Primary Examiner* — Jafar Parsa
(74) *Attorney, Agent, or Firm* — Frank Rosenberg

(57) ABSTRACT

The present invention provides an improved process for removing heat from an exothermic reaction. In particular, the present invention provides a process wherein heat can be removed from multiple reaction trains using a common coolant system.

11 Claims, 5 Drawing Sheets

(56) References Cited

U.S. PATENT DOCUMENTS

| | | | |
|---|---|---|---|
| 8,747,805 | B2 | 6/2014 | Tonkovich et al. |
| 9,006,298 | B2 | 4/2015 | LeViness et al. |
| 9,108,904 | B2 | 8/2015 | Brophy et al. |
| 9,174,387 | B2 | 11/2015 | Luzenski et al. |
| 2003/0087971 | A1 | 5/2003 | Steynberg |
| 2004/0192989 | A1* | 9/2004 | Espinoza .................. B01J 8/06 518/706 |
| 2005/0175519 | A1 | 8/2005 | Rogers et al. |
| 2009/0010821 | A1 | 1/2009 | Lehr |
| 2012/0148455 | A1* | 6/2012 | Morrow ............... B01J 19/0013 422/187 |
| 2013/0306299 | A1 | 11/2013 | Morita et al. |

OTHER PUBLICATIONS

Written Opinion of the International Searching Authority from International Application No. PCT/GB2015/053131 dated Jan. 23, 2017.

Examination Report dated Dec. 7, 2017 in DE Application No. 112015004756.5.

Notification of Reason for Refusal from JP Patent Application 2017-522533 dated Jan. 25, 2018.

\* cited by examiner

PROCESS OF REMOVING HEAT

RELATED APPLICATIONS

This application is a divisional of U.S. patent application Ser. No. 14/918,314, filed Oct. 20, 2015, now U.S. Pat. No. 9,822,049, which claims the benefit of priority U.S. Provisional Patent Application Ser. No. 62/066,233, filed Oct. 20, 2014.

The present invention provides an improved process for removing heat from an exothermic reaction. In particular, the present invention provides a process wherein heat can be removed from multiple reaction trains using a common coolant system.

BACKGROUND

A number of commercially useful reactions are exothermic in nature and generate large amounts of heat which needs to be removed. On an industrial scale, for many reactions, it is possible to remove the heat of reaction in the form of a circulating fluid, such as water, which is raised for steam, which can then be used for another purpose, for example, for generating power.

An example of such a reaction is the Fischer Tropsch (FT) reaction which converts synthesis gas (syngas) to linear hydrocarbons. The heat of reaction may be removed by partially vaporising boiler feed water (BFW) which is introduced into thermal contact with and receives heat given off by the exothermic FT reaction vessel, tubes, or channels wherein the FT catalyst is contained and the reaction with syngas takes place. Temperature is one of the most critical operating parameters of the FT reaction, controlling the carbon monoxide conversion present in the syngas (per pass CO conversion), in addition to the length of hydrocarbon chains synthesized (selectivity).

The temperature of the coolant is selected to provide the desired cooling capacity for the reaction. In the case where vaporisation of water is used to cool the reaction, the temperature of the coolant is controlled by the pressure at which the steam is generated. Coolant which is partially vaporised as a consequence of the exothermic reaction is passed from a reactor to a reservoir, essentially a steam drum, where the vapour and liquid are separated. The vapour (steam) may be further used for heating or power generation. The liquid may be used further in the process or treated and/or recirculated as a coolant in the process. The pressure at which the steam drum is operated dictates the saturation temperature of the liquid, which is then recycled back into the reactor as coolant.

In an industrial process, there is always a drive to maximize the production capacity of a reaction train in order to exploit economics of scale to minimize unit cost of production. The practical limit of production capacity of a single reaction train may be driven by the maximum size of major equipment or other factors. Thus, in order to meet the overall desired production capacity of a facility, multiple reaction trains may be required. When multiple reaction trains are used, it is commonly desired to optimize the output and maximize the ease of operation of each reaction train used with the associated duplication of equipment for independent operation.

In the case of a conventional exothermic catalytic process, in particular, where the activity of the catalyst declines over time, each reaction train is designed to operate independently at maximum production capacity, with an operating strategy for different reactor temperatures in different trains as the reaction catalyst activity declines over time and is compensated for by increasing the reaction temperature. In this case, the coolant temperature profiles may be different between multiple trains in order to optimize production. In the case of a process cooled by vaporisation of water, such as a Fischer-Tropsch (FT) process, reaction temperature is controlled by the pressure of the resulting steam, which is typically sent to a separate vessel ("steam drum") in which the pressure of the steam is controlled. In this case, the temperature and pressure of the steam drum may be different at any point in time for each reaction train. To date, the FT process has been designed so as to utilise a single steam drum per reaction train. This means that the reaction temperature of each reaction train can be controlled by the operating pressure of the associated single steam drum. A similar approach has been adopted in other exothermic industrial processes where the heat of reaction can be controlled by a recirculating coolant, such as the generation of steam from water.

SUMMARY OF INVENTION

For industrial processes, there is always a drive to optimise the process from an economic perspective. Any change which can be made to reduce costs while maintaining an acceptable yield, conversion and/or selectivity is a major positive in this field.

It is with this in mind that the inventors have surprisingly found a way of obtaining a significant economical benefit when operating an exothermic process in which the reaction temperature can be controlled by the transfer of heat to a recirculating coolant. More specifically, the present inventors have found that even where there are multiple reaction trains, it is possible to remove the heat of reaction using a single common coolant reservoir rather than using a separate coolant reservoir for each reaction train. This greatly reduces the amount of equipment which is required thus significantly reducing costs.

However, it is entirely counter-intuitive that making this change will bring economical benefits which outweigh the reduction in output associated with separate temperature control of different reaction trains. Prior to this invention, the perceived wisdom in the field has been that it is necessary to include a separate coolant reservoir for each reaction train. More specifically, the impetus has been optimize the production capacity of each reaction train by individually controlling the reaction temperature in each reaction train, which may vary between trains due to differences in operating history, including such factors as catalyst deactivation, scheduled or unscheduled maintenance, and optimization of on-stream factors by ensuring that reactor trains can be operated independently.

For exothermic reactions, such as the FT reaction, where temperature is a critical operating parameter, it is surprising that it is still possible to obtain acceptable conversions and selectivities when using a single coolant reservoir as it means that all of the reaction trains must be operated at the same temperature and pressure, specifically that which is dictated by the single common coolant reservoir. However, the present inventors have found that the performance of the exothermic reaction in each reaction train can alternatively be controlled by altering the flow rate of the reactants through the reaction train whilst maintaining a common coolant reservoir condition of temperature and pressure. Thus, it is possible to control each reaction train individually, as is possible using conventional methods.

As used herein, the term "same temperature and pressure" means a deviation of ±10 psi or less in pressure and ±10° C. or less in temperature.

Accordingly, the present invention provides a method for removing heat from an exothermic reaction comprising:
(a) dividing a reactant feed stream into at least two separate reactant substreams;
(b) feeding each reactant substream into a separate reaction train which comprises a reactor;
(c) feeding a coolant stream from a common coolant reservoir into each reactor;
(d) performing the exothermic reaction in the reactor to produce reaction products and coolant to which heat has been transferred;
(e) feeding the coolant to which heat has been transferred from each reaction train to a single common reservoir in which the heat is removed from the coolant;
(f) feeding the coolant from which the heat has been removed in step (e) back into step (c), wherein:
each of the reactors in step (b) are operated at the same temperature and pressure; and
the progress of the exothermic reaction in each reactor is controlled by adjusting the flow rate of the reactant substream through the reaction train of which the reactor forms a part and/or by adjusting the composition of the reactant substream which is fed into each reaction train.

Thus, it is clear that, although the process involves the use of multiple reaction trains, the coolant to which heat has been transferred from each reaction train is passed to a single common coolant reservoir. Instead of using temperature as a key control, the progress of the exothermic reaction in each reactor is controlled by adjusting the flow rate of the reaction train or by adjusting the composition of the reactant substream which is fed to each reactor. Advantageously, the process of the present invention reduces the amount of equipment which is required, hence reducing the associated costs.

A further advantage of the method of the present invention is that where there are at least three reaction trains, it is possible to isolate and then subsequently reintroduce one of the reaction trains from the process while having minimal impact on the operating conditions of the remaining reaction trains. This means that a reaction train can be isolated for catalyst regeneration or reloading without having to stop the whole process. Again, this has a significant economic advantage.

Steps (a)-(f)
Step (a)

In the first step (step (a)) of the method of the present invention, a reactant feedstream is divided into at least two reactant substreams and each substream is then fed to a separate reaction train. Separating the reactant feedstream in this way ensures that the extent of reaction which occurs is maximised.

In one embodiment, the reactant feedstream is divided into at least 3, 4, 5, 6, 7, 8, 9, 10, 11, etc. feedstreams. In this regard, the only limitation on the number of substreams into which the reactant feedstream is divided is the complexity (and cost) of the resulting apparatus. The greater the number of reactant substreams, and hence reaction trains, the more straightforward it becomes to isolate one of the reaction trains while having minimal impact on the reaction trains which remain in operation. Typically, the reactant feedstream is divided into between 2 and 8 feedstreams.

The nature of the reactant feedstream will depend on the nature of the exothermic reaction. The terms "exothermic reaction" are used to describe a chemical reaction which produces heat. In particular, the method of the present invention is useful for any exothermic reaction in which the heat of reaction can be controlled by the transfer of heat to a coolant Examples of suitable exothermic reactions include the Fischer-Tropsch process, methanol production, ethylene oxide production, dimethyl ether (DME) production, vinyl acetate (VAM) production, hydroprocessing including hydrotreating, hydrocracking, oxidations, including partial oxidations, oxidative coupling, alkane oxidation, alkylation, isomerization, ammonia synthesis, water-gas-shift and hydrogenation. The exothermic reactions with which the present invention is concerned are well known and well documented such that the skilled person would be familiar with suitable reactants and reaction conditions.

The method of the present invention is particularly applicable to heterogeneously catalysed reactions where the activity of the catalyst decreases with time. For such reactions, conventionally, it would have been necessary to increase temperature to maintain output but the method of the present invention provides a way in which this can be avoided.

Where the exothermic reaction is a Fischer-Tropsch reaction, the reactant feedstream will comprise a gaseous mixture that contains CO and $H_2$. This mixture is often referred to as "synthesis gas" or "syngas". The reactant feedstream may comprise $H_2$ and CO with a molar ratio of $H_2$ to CO in the range from about 1:1 to about 4:1, more preferably 1.4:1 to about 2.1:1, or from about 1.5:1 to about 2.1:1, or from about 1.6:1 to about 2:1, or from about 1.6:1 to about 1.9:1. The reactant feedstream may be comprised entirely of fresh synthesis gas or may alternatively comprise a mixture of fresh synthesis gas and recycled tail gas (which also contains CO and $H_2$). In one embodiment, the reactant feedstream may comprise 0 to 50%, alternatively 4 to 15% by weight of inert components (i.e. components which are not CO or $H_2$).

Similarly, where the exothermic reaction is methanol production, the reactant feedstream will comprise synthesis gas. In this case, the reactant feedstream may comprise $H_2$ and CO with a molar ratio of $H_2$ to CO in the range from 0.5 to 4, alternatively from 1 to 2.5. The reactant feedstream may be comprised entirely of fresh synthesis gas or may alternatively comprise a mixture of fresh synthesis gas and recycled tail gas (which also comprises CO and $H_2$). In one embodiment, the reactant feedstream may comprise 0 to 50%, alternatively 4 to 15% by weight of inert components (i.e. components which are not CO or $H_2$ e.g. $N_2$, $CO_2$ etc).

As used herein, the term "tail gas" means the gas stream leaving the reactor following the exothermic reaction. For example, where the exothermic reaction is a Fischer-Tropsch reaction, the tail gas comprises unconverted syngas, vapor-phase by-products of the Fischer-Tropsch reaction and inert components.

Where the exothermic reaction is ethylene oxide production, it is generally produced by the oxidation of ethylene using oxygen over a catalyst (typically a silver catalyst) and the reactant feedstream will comprise a mixture of ethylene and oxygen. The reactant feedstream may comprise ethylene and oxygen with a molar ratio of ethylene to oxygen of less than about 4:1, in one embodiment less than about 3:1. The molar ratio of ethylene to oxygen may be in the range from 0.2:1 to about 4:1 or from about 0.5:1 to about 3:1 or from about 1:1 to about 3:1.

In an embodiment where the exothermic reaction is dimethyl ether DME production, where the DME is produced by direct reaction of syngas to DME or by dehydration of methanol over a dehydration catalyst, the reactant feedstream comprises methanol. Alternatively, the DME may be produced by a process that integrates methanol synthesis and dehydration into a single reactor, in which case the reactant feed stream comprises synthesis gas.

In one embodiment, the exothermic reaction is a hydrocracking reaction. Hydrocracking requires the reaction between hydrogen and one or more hydrocarbon reactants. The hydrocarbons may comprise any hydrocarbon that can be hydrocracked including saturated aliphatic compounds (e.g. alkanes), unsaturated aliphatic compounds (e.g. alkenes, alkynes), hydrocarbyl (e.g. alkyl) substituted aromatic compounds, hydrocarbylene (e.g. alkylene) substituted aromatic compounds and the like. In this case, the reactant feedstream may comprise one or more hydrocarbon reactants that may vary from naphtha to heavy crude oil residual fractions. In this regard, the feed composition may have a 5% by volume boiling point above about 175° C., and in one embodiment above about 205° C. In one embodiment, at least about 90% by volume of the feed composition may fall within the boiling point range of about 150° C. to about 570° C., and in one embodiment from about 320° C. to about 540° C. The feed composition may comprise one or more petroleum fractions such as atmospheric and vacuum gas oils (AGO and VGO). The feed composition may comprise one or more mineral or synthetic oils, or a mixture of one or more fractions thereof. The feed composition may comprise one or more straight run gas oils, vacuum gas oils, demetallized oils, deasphalted vacuum residues, coker distillates, cat cracker distillates, shale oil, tar sand oil, coal liquids, or a mixture of two or more thereof, and the like. The ratio of hydrogen to hydrocarbon reactant in the reactant substream which is fed to the reaction train may be in the range from about 10 to about 1000 standard cubic centimeters (sccm) of hydrogen per cubic centimeters (ccm) of hydrocarbon reactant, or in the range from about 100 to about 500 sccm/cm.

Where the exothermic reaction is VAM production, the reactant feedstream may comprise ethylene, acetic acid and dioxygen. In one embodiment, the ratio of ethylene to acetic acid to dioxygen in the reactant feedstream may be in the range from about 6:3:1 to about 2:2:1.

Where the exothermic reaction is oxidation of a hydrocarbon reactant to an oxygenate or a nitrile, the reactant feedstream may comprise a hydrocarbon reactant, oxygen or a source of oxygen and optionally ammonia. The term "hydrocarbon reactant" refers to any hydrocarbon compound that is capable of undergoing an oxidation or ammoxidation reaction and is a fluid at the temperature and pressure at which the reactor is operated. Examples include saturated aliphatic compounds (e.g. alkanes), unsaturated aliphatic compounds (e.g. monoenes, polyenes), aldehydes, alkyl substituted aromatic compounds, alkylene substituted aromatic compounds. The term "oxygenate" refers to a hydrocarbon product which contains at least one oxygen atom (CO and $CO_2$ are excluded). Examples include alcohols (e.g. methanol, ethyl alcohol), epoxides (e.g. ethylene oxide), aldehydes (e.g. formaldehydes, acrolein), carboxylic acids (e.g. acetic acid, acrylic acid), carboxylic acid anhydrides (e.g. maleic anhydride), esters (e.g. vinyl acetate). The mole ratio of the hydrocarbon reactant to oxygen may be in the range from about 0.2:1 to about 8:1 or from about 0.5:1 to about 4:1, or from about 1:1 to about 3:1. The ammonia may be obtained from any source. Where it is present, the mole ratio of the hydrocarbon reactant to ammonia may range from about 0.5:1 to about 5:1 or from about 0.5:1 to about 2:1.

In one embodiment, the exothermic reaction is the oxidation of methanol to formaldehyde. In this embodiment, the reactant feedstream comprises methanol and oxygen.

Step (b)

In step (b) of the method of the present invention, each reactant substream is fed into a separate reaction train. Each reaction train comprises at least one reactor. In order to maximise the extent of reaction, it may be advantageous for each reactant train to comprise multiple reactors. Where multiple reactors are present, they may be arranged in series or in parallel. Preferably the multiple reactors are arranged in parallel. In some embodiments, for example where the exothermic reaction is a FT reaction, the multiple reactors are arranged in parallel.

The nature of the reactors is not limited. In one embodiment, the reactor may be selected from the group consisting of a conventional fixed bed reactor, a fluidised bed reactor, a slurry phase reactor and a microreactor.

The skilled person will be familiar with suitable conventional fixed bed reactors. Commercial conventional fixed bed reactors are made up of multiple, in some cases hundreds or thousands of long (up to 10 meters), narrow reactor tubes which are welded onto "tube plates" and which are filled with packing material which comprises catalyst, thus forming a bed of catalyst through which the reactant substream flows. The tubes may have a diameter in the range from 20 to 50 mm. The catalyst may be in the form of pellets having a diameter in the range from 1 to 5 mm. The catalyst particles may be designed to be uneven shapes in order to reduce their packing efficiency within the reactor tubes and prevent undue pressure drop. The length of the reactor tubes means that the conversion of the exothermic reaction is maximised because the reactant substream is in contact with the catalyst for an increased time.

The skilled person will also be familiar with fluidised bed reactors. There are two types of fluidised bed reactor. In a fixed fluidised bed reactor (FFB), the catalyst bed is contained within the reactor vessel. In a circulating fluidised bed (CFB), the catalyst is entrained in the gas flow and is carried around a loop.

In fixed fluidised bed reactors, the reactant substream is passed through the catalyst bed (comprised of catalyst particles) at a sufficient velocity to cause the bed to fluidise. The catalyst particles are typically much smaller than those used in a fixed bed reactor in order to enable them to be fluidised at reasonable gas velocities. Within the top of the reactor, cyclones disengage the catalyst particles and return them to the bed while the product stream flows through the condensing train. Cooling coils are arranged with the reactor to remove heat. The suspended particles are in intimate contact with the gas stream and the cooling coils. In a fixed fluidisied bed reactor, the catalyst particles are moving at high velocities and experience regular collisions which causes them to physically break down into a powder. This means that the catalyst particles have to be replaced on a continuous basis.

As the skilled person will be aware, in a slurry phase reactor, the reactant substream is passed through a slurry made up of a powdered supported catalyst. The catalyst typically comprises solid catalyst particles having a diameter in the range from 0.05 to 0.3 mm. Where the reactant stream is a gas which is introduced at the bottom of the reactor and then rises up through the slurry, the reactor is known as a bubble column reactor. Slurry phase reactors are advantageous because they provide excellent temperature control and close to isothermal operation with no temperature gradients. However, liquid products formed in the reactor must be filtered after removal from the slurry bed in order to ensure that all of the catalyst particles have been removed.

In one embodiment, the reactor is a microchannel reactor. The term "microchannel reactor" refers to an apparatus comprising one or more process microchannels wherein a reaction process is conducted. In particular, the microchannel reactor may comprise at least one, preferably a plurality of process microchannels in thermal contact with at least one, preferably a plurality of heat exchange channels. Where a catalyst is present, it is contained within the process microchannels.

Examples of suitable microchannel reactors are described in WO2014/026204, the contents of which is incorporated herein by reference.

In particular, the microchannel reactor may comprise one or more slots for receiving one or more catalyst inserts (e.g., one or more fins or fin assemblies, one or more corrugated inserts, etc.) wherein the process microchannels comprise the slots, are positioned in the catalyst inserts, and/or comprise openings formed by the walls of the slots and the inserts. When two or more process microchannels are used, the process microchannels may be operated in parallel. The microchannel reactor may include a header or manifold assembly for providing for the flow of fluid into the one or more process microchannels, and a footer or manifold assembly providing for the flow of fluid out of the one or more process microchannels. The microchannel reactor may comprise one or more heat exchange channels adjacent to and/or in thermal contact with the one or more process microchannels. The heat exchange channels may provide cooling for the fluids in the process microchannels. The heat exchange channels may be microchannels. The microchannel reactor may include a header or manifold assembly for providing for the flow of heat exchange fluid into the heat exchange channels, and a footer or manifold assembly providing for the flow of heat exchange fluid out of the heat exchange channels.

The term "microchannel" refers to a channel having at least one internal dimension of height or width of up to about 10 millimeters (mm), and in one embodiment up to about 5 mm, in one embodiment up to about 2 mm, in one embodiment up to about 1 mm. The microchannel may comprise at least one inlet and at least one outlet wherein the at least one inlet is distinct from the at least one outlet. The microchannel may not be merely an orifice. The microchannel may not be merely a channel through a zeolite or a mesoporous material. The length of the microchannel may be at least about two times the height or width, and in one embodiment at least about five times the height or width, in one embodiment at least about ten times the height or width. The internal height or width of the microchannel may be in the range of about 0.05 to about 10 mm, or from about 0.05 to about 5 mm, or from about 0.05 to about 2 mm, or from about 0.05 to about 1.5 mm, or from about 0.05 to about 1 mm, or from about 0.05 to about 0.75 mm, or from about 0.05 to about 0.5 mm, or from about 1 to about 10 mm, or from about 2 to about 8 mm, or from about 3 to about 7 mm. The other internal dimension of height or width may be of any dimension, for example, up to about 3 meters, or about 0.01 to about 3 meters, and in one embodiment about 0.1 to about 3 meters, or about 1 to about 10 mm, or from about 2 to about 8 mm, or from about 3 to about 7 mm. The length of the microchannel may be of any dimension, for example, up to about 10 meters, and in one embodiment from about 0.1 to about 10 meters, and in one embodiment from about 0.2 to about 10 meters, and in one embodiment from about 0.2 to about 6 meters, and in one embodiment from 0.2 to about 3 meters. The microchannel may have a cross section having any shape, for example, a square, rectangle, circle, semi-circle, trapezoid, etc. The shape and/or size of the cross section of the microchannel may vary over its length. For example, the height or width may taper from a relatively large dimension to a relatively small dimension, or vice versa, over the length of the microchannel.

The term "adjacent" when referring to the position of one channel relative to the position of another channel may mean directly adjacent such that a wall or walls separate the two channels. In one embodiment, the two channels may have a common wall. The common wall may vary in thickness. However, "adjacent" channels may not be separated by an intervening channel that may interfere with heat transfer between the channels. One channel may be adjacent to another channel over only part of the dimension of the another channel. For example, a process microchannel may be longer than and extend beyond one or more adjacent heat exchange channels.

The term "thermal contact" refers to two bodies, for example, two channels, that may or may not be in physical contact with each other or adjacent to each other but still exchange heat with each other. One body in thermal contact with another body may heat or cool the other body.

The term "fluid" refers to a gas, a liquid, a mixture of a gas and a liquid, or a gas or a liquid containing dispersed solids, liquid droplets and/or gaseous bubbles. The droplets and/or bubbles may be irregularly or regularly shaped and may be of similar or different sizes.

Catalyst

The reactor may comprise a catalyst. Preferably the catalyst is a heterogeneous catalyst. In one embodiment, the catalyst may be in the form of particulate solids.

Where the reactor is a microchannel reactor as described above, the catalyst may be used as a particulate solid loaded into the process channels, or coated on interior walls of the process microchannels or grown on interior walls of the process microchannels. The catalyst may be supported on a support having a flow-by configuration, a flow-through configuration or a serpentine configuration. The catalyst may be supported on a support having the configuration of a foam, felt, wad, fin or a combination of two or more thereof. Alternatively, the catalyst may be in the form of insert which may be fitted within a suitable slot within the reactor.

The skilled person will be familiar with catalysts suitable for performing different exothermic reactions.

In particular, where the exothermic reaction is a Fischer-Tropsch process, preferably the catalyst may be derived from a catalyst precursor comprising cobalt, a promoter such as Pd, Pt, Rh, Ru, Re, Ir, Au, Ag and/or Os and a surface modified support, wherein the surface of the support has been modified by being treated with silica, titania, zirconia, magnesia, chromia, alumina or a mixture of two or more thereof. In one embodiment, the catalyst precursor may comprise a cobalt oxide, in particular $Co_3O_4$. Suitable support materials include a refractory metal oxide, carbide, carbon, nitride or a mixture of two or more thereof. The support may comprise alumina, zirconia, silica, titania, or a mixture of two or more thereof. In one embodiment, the support may comprise a $TiO_2$ modified silica support wherein the support contains at least about 11% by weight $TiO_2$, or from about 11 to about 30% by weight $TiO_2$, or from about 15 to about 17% by weight $TiO_2$, in one embodiment, about 16% by weight $TiO_2$. The surface of the surface-modified support may be amorphous.

In an embodiment where the exothermic reaction is methanol production, preferably the catalyst is a copper-based catalyst, for example $Cu/ZnO/Al_2O_3$.

In an embodiment where the exothermic reaction is ethylene oxide production, preferably the catalyst may comprise a metal, metal oxide or mixed metal oxide of a metal selected from Mo, W, V, Nb, Sb, Sn, Pt, Pd, Cs, Zr, Cr, Mg, Mn, Ni, Co, Ce or a mixture of two or more thereof. These catalysts may also comprise one or more alkali metals or alkaline earth metals or other transition metals, rare earth metals or lanthanides. Elements such as P and Bi may be present. The catalyst may be supported and, if so, useful support materials include metal oxides (e.g. alumina, titania, zirconia), silica, mesoporous materials, zeolites, refractory materials or combinations of two or more thereof. In particular, the catalyst may be any one of the catalysts disclosed in U.S. Pat. No. 5,597,773, U.S. Pat. No. 5,703,253, U.S. Pat. No. 5,705,661, U.S. Pat. No. 6,762,311 and EP0266015, the contents of which are incorporated herein by reference.

In an embodiment where the exothermic reaction is DME production, the catalyst may be a blend of a methanol synthesis catalyst, for example $Cu/ZnO/Al_2O_3$ and a dehydration catalyst, e.g. $g-Al_2O_3$.

In an embodiment where the exothermic reaction is hydrocracking, the catalyst may include zeolite catalysts including beta zeolite, omega zeolite, L-zeolite, ZSM-5 zeolites and Y-type zeolites. The hydrocracking catalyst may comprise one or more pillared clays, MCM-41, MCM-48, HMS, or a combination of two or more thereof. The hydrocracking catalyst may comprise Pt, Pd, Ni, Co, Mo, W, or a combination of two or more thereof. The hydrocracking catalyst may include a refractory inorganic oxide such as alumina, magnesia, silica, tilania, zirconia and silica-alumina. The hydrocracking catalyst may comprise a hydrogenation component. Examples of suitable hydrogenation components include metals of Group IVB and Group VIII of the Periodic Table and compounds of such metals. Molybdenum, tungsten, chromium, iron, cobalt, nickel, platinum, palladium, iridium, osmium, rhodium and ruthenium may be used as the hydrogenation component. These catalysts are described in U.S. Pat. No. 6,312,586 B1, which is incorporated herein by reference.

In an embodiment where the exothermic reaction is hydrotreating, the hydrotreating catalyst may be any hydrotreating catalyst. The hydrotreating catalyst may comprise Ni, Mo, Co, W, or combinations of two or more thereof supported on alumina. The catalyst may comprise $Mo-W/Al_2O_3$.

In an embodiment where the exothermic reaction is the production of VAM, the catalyst may comprise Pd, Au and, in some embodiments, potassium acetate (KOAc). Examples of suitable catalysts are described in U.S. Pat. No. 3,743,607, U.S. Pat. No. 3,775,342, U.S. Pat. No. 5,557,014, U.S. Pat. No. 5,990,334, U.S. Pat. No. 5,998,659, U.S. Pat. No. 6,022,823, U.S. Pat. No. 6,057,260 and U.S. Pat. No. 6,472,556, all of which are incorporated herein by reference. The catalysts used preferably contain a refractory support, preferably a metal oxide such as silica, silica-alumina, titania or zirconia. In one embodiment, the catalyst comprises more than 2 wt % Pd, more than 4 wt % Pd, more than 10 wt % Pd and in some embodiments, at least 12 wt % Pd.

In an embodiment where the exothermic reaction is hydrocarbon oxidation, the catalyst may comprise a metal, metal oxide or mixed metal oxide of a metal selected from Mo, W, V, Nb, Sb, Sn, Pt, Pd, Cs, Zr, Cr, Mg, Mn, Ni, Co, Ce or a mixture of two or more thereof. These catalysts may also comprise one or more alkali metals or alkaline earth metals or other transition metals, rare earth metals or lanthanides. Elements such as P and Bi may be present. The catalyst may be supported and, if so, useful support materials include metal oxides (e.g. alumina, titania, zirconia), silica, mesoporous materials, zeolites, refractory materials or combinations of two or more thereof.

In an embodiment where the exothermic reaction is the oxidation of methanol to form formaldehyde, the catalyst may be a Fe—Mo-Ox catalyst.

Step (c)

In step (c) of the method of the invention, a coolant is fed into the reactors in each reaction train. The coolant fed into each reaction train is derived from a common coolant reservoir. In this regard, there is a single coolant circulation network which feeds into all of the reaction trains. The coolant is comprised of fresh coolant and coolant recycled from the steam drum in step (e).

Alternatively, where there are three or more reaction trains, at least two of the reaction trains may be fed coolant in step (c) from a single coolant circulation network while the remaining reaction trains are fed coolant from one or more different coolant circulation networks. In such an embodiment, there will be multiple coolant reservoirs. However, the total number of coolant reservoirs will always be lower than the total number of reaction trains.

The coolant may be selected from the group consisting of a fluid which at least partially vaporizes as a consequence of the transfer of heat from the exothermic reaction which takes place in the reactor and a hot oil. As will be appreciated by the skilled person, the choice of coolant will depend on the exothermic reaction and, in particular, the temperatures reached in the reactor in which the exothermic reaction takes place.

The fluid which is partially vaporized may be a single component coolant fluid, such as water, propane, butane, pentane, hexane, ammonia, an alcohol, or a higher hydrocarbon. Alternatively, the fluid which is partially vaporized may be a coolant mixture comprising one or more single component fluids. Examples of a coolant mixture include ammonia-water or a mixed solvent.

In one embodiment, the coolant is a fluid which at least partially vaporizes as a consequence of the transfer of heat from the exothermic reaction which takes place in the reactor. Where this is the case, the coolant is a fluid which has a boiling point lower than the temperature reached in the reactor. Preferably, the coolant is water. Where the coolant is water, the heat transferred from the exothermic reaction causes the water to at least partially vaporize, thus generating steam. This steam can be recovered and used elsewhere in the process or even to produce electricity. It is particularly preferred to use water as a coolant where the temperature of the exothermic reaction is in the range from 80 C to 450 C, or more preferably 100 C to 300 C. Another example of suitable coolants which fall within this group i.e. which at least partially vaporize during the process, are organic solvents such as those described in WO2013/055864, the contents of which is incorporated herein by reference.

The coolant which is fed to the reactors may be at a temperature in the range from about 40 C to about 400° C., preferably in the range from about 100 C to about 250 C.

The coolant may either be fed to the reactors at a constant flow or the flow may be adjusted depending upon the release of heat which, in turn, depends on the rate at which the reactant feedstream is fed to the reactor(s).

The coolant may be subcooled by either direct (mixing) or indirect heat exchange to maintain the desired CO conversion rate or product selectivity.

Where the reactor is a microchannel reactor as described previously, the coolant is fed into the heat exchange channels which are in thermal contact with the process channels.

Step (d)

As the reactant substream flows along the reaction train and through the one or more reactors, it is contacted with the catalyst and the exothermic reaction takes place (step (d)). The heat generated by the exothermic reaction is transferred to the coolant, thus removing the heat from the reaction. Hence, step (d) produces reaction products and coolant to which heat has been transferred. Where the coolant is a hot oil, it absorbs the heat by expansion rather than by vaporization. Where the coolant is a fluid which has a boiling point lower than the heat generated by the exothermic reaction, it removes heat from the reaction by undergoing a partial phase change, for example, where water is the coolant, steam is generated.

Reaction Products

Where the exothermic reaction is a Fischer-Tropsch process, the reaction products comprise hydrocarbons (which are predominantly aliphatic) and water. The term "aliphatic hydrocarbons" is used to describe an aliphatic hydrocarbon having 2 or more carbon atoms, or 3 or more carbon atoms, or 4 or more carbon atoms, or 5 or more carbon atoms, or 6 or more carbon atoms. The higher molecular weight aliphatic hydrocarbons may have up to about 200 carbons atoms, up to about 150 carbons atoms, up to about 100 carbon atoms, up to about 90 carbon atoms, up to about 80 carbon atoms, up to about 70 carbon atoms, up to about 60 carbon atoms, up to about 50 carbon, up to about 40 carbon atoms or up to about 30 carbon atoms. Examples may include ethane, propane, butane, pentane, hexane, octane, decane, dodecane and the like.

In an embodiment where the exothermic reaction is methanol production, the reaction products comprise methanol, hydrogen and water.

In an embodiment where the exothermic reaction is ethylene oxide production, the reaction products comprise ethylene oxide, carbon dioxide and water.

In an embodiment where the exothermic reaction is DME production, the reaction products comprise DME and carbon dioxide.

In an embodiment where the exothermic reaction is hydrocracking, the reaction products comprise two or more hydrocarbon products having lower molecular weights than the hydrocarbon reactant.

In an embodiment where the exothermic reaction is the production of VAM, the reaction products comprise vinyl acetate monomer and water.

In an embodiment where the exothermic reaction is hydrocarbon oxidation, the reaction products comprise an oxygenate product.

In an embodiment where the exothermic reaction is formaldehyde production, the reaction products comprise formaldehyde.

Step (e)

In step (e), the coolant to which heat has been transferred from each of the reaction trains is fed to a common single coolant reservoir. In the reservoir, the heat absorbed from the exothermic reaction is removed and the coolant is returned to its original state. The coolant can then be recycled back into step (c).

The person skilled in the art will be familiar with suitable reservoirs. In particular, depending on the nature of the coolant, the reservoir may be a heat exchanger, for example where the coolant is a hot oil. Alternatively, where the coolant is one which has been at least partially vaporized, the reservoir may comprise a phase separator for removing the heat in the form of a vapor. An example of such a reservoir is a steam drum.

Where the heat of the exothermic reaction has been removed in step (d) by partial vaporization of the coolant, the vapor and liquid phases are separated in the reservoir, the vapor is removed and the liquid is recycled back as coolant into step (c). In this situation, it may be necessary to add fresh coolant to the stream which is fed back into step (c) to compensate for the coolant which has been lost as vapor. For example, where the coolant is water, the reservoir is a steam drum wherein steam and water are separated. The recovered water is recycled back into step (c) as coolant and topped up with fresh water to compensate for the water which has been lost in the form of steam. The steam may be condensed and returned to the coolant system.

The conditions, in particular the pressure, under which this single common coolant reservoir is operated dictate the saturation temperature of the liquid which is then recycled to the reactor as coolant and hence dictate the operating temperature and pressure of each of the reaction trains. Where the coolant is a hot oil which expands rather than vaporizes in response to the transfer of heat from the exothermic reaction, it is the temperature under which the single common coolant reservoir is operated which dictates the operating temperature of each of the reaction trains. Hence, all of the reactors in the method of the present invention are operated at the same temperature and pressure.

In one embodiment, the coolant is a fluid which is partially vaporized as a consequence of the transfer of heat from the exothermic reaction, preferably water and the reservoir is a steam drum.

The common single coolant reservoir may be operated at a temperature in the range from about 25 to about 300° C., from about 100 to about 300° C., or about 200 to about 225° C., or about 200 to about 220° C., or about 205° C. The common single coolant reservoir may be operated at a pressure in the range from about 100 to about 15,000 kPa, or about 100 to about 8600 kPa, or about 450 to about 4100 kPa, or about 450 to about 3400 kPa, or about 1200 to about 2600 kPa, or about 1200 to 2100 kPa, or about 1200 to about 1900 kPa.

In one embodiment, the common single steam drum is operated at a temperature in the range from 100 to 300° C., in one embodiment (for example where the exothermic reaction is a FT process) 200 to 225° C., or 200 to 220° C., or about 205° C. and a pressure in the range from about 100 to about 8600 kPa, about 100 to about 3400 kPa, in one embodiment, about 1200 to about 2600 kPa, or about 1200 to about 2100 kPa, or about 1200 to about 1900 kPa, or about 1700 to about 1900 kPa.

Controlling the Progress of the Exothermic Reaction

The use of a common single coolant reservoir means that temperature of the individual reaction trains (which is the usual variable used) cannot be used to control the performance of the exothermic reaction which is taking place in each of the reactors. This being the case, the present inventors have surprisingly found that it is possible to obtain an acceptable degree of control over the different reaction trains by controlling the flow rate (or Gas Hourly Space Velocity (GHSV)) of the reactant substream through each reaction train.

The GHSV of the reactant substream is conventionally defined as the volumetric flow of reactant at normal pressure and temperature divided by the bulk volume of catalyst through which it is flowing. The GHSV of the reactant substream can be measured by conventional techniques, specifically by measuring the flow rate of the reactant substream to the reactor and then by dividing this value by the volume of the catalyst.

A means of adjusting the flow rate of the reactant substream may be provided in at least one of the reaction trains. Preferably, a separate means of adjusting the flow rate of the reactant substream is provided in each of the reaction trains allowing the flow rate of each reactant substream to be adjusted independently. The means of adjusting the flow rate may be a valve, e.g. an automated control valve, preferably an automated flow control valve.

The flow rate of a reactant substream may be adjusted to account for factors such as the deactivation of the catalyst in the reactor present in that reaction train. Catalyst deactivation leads to a reduction in catalytic activity over time. The method of the present invention may be used to reduce the flow rate of the reactants to a particular reactor in line with the deactivation of the catalyst in order to adjust the conversion upward to compensate for such catalyst deactivation, to ensure each reaction train meets the desired CO conversion rate or product selectivity. The catalysts in different reaction trains may be at different stages of deactivation. The ability to independently adjust the flow rates of the reactant substreams in each reaction train provides a means to ensure that each reaction train is operating at the desired CO conversion rate or product selectivity, regardless of any difference in the stage of deactivation of the catalysts.

The flow rate of the reactant substream can be determined by reference to the desired contact time of the reactants with the catalyst. The term "contact time" refers to the volume of a reaction zone, i.e. the space within a reactor where the exothermic reaction occurs, divided by the volumetric flow rate of the reactant substream at a temperature of 0° C. and a pressure of one atmosphere.

To maintain a constant reaction within a reactor, specifically a microchannel reactor, any flow rate adjustments to a particular reactant substream should ensure a contact time of the reactants with the catalyst of from about 10 to about 2000 milliseconds (ms), or from about 10 ms to about 1000 ms, or from about 20 ms to about 500 ms, or from about 200 ms to about 400 ms, or from about 240 ms to about 350 ms.

Alternatively or in addition, the present inventors have also found that the extent of the exothermic reaction can be controlled by altering the composition of the reactant substream to each reaction train. In some embodiments, the reactant substream may be comprised of reactants obtained from different sources. For example, in one embodiment, the reactant substream may comprise both fresh reactants and recycled reactants. The recycled portion of the reactant substream may have a different composition to the fresh feed, in particular in relation to the amount of inerts which are present. Hence, one way in which the composition of the reactant substream may be altered is to alter the proportion of the reactant substream which is made up from recycled reactants. In a different embodiment, the reactant substream may be comprised of fresh reactant and reactants which have been obtained from an upstream process. For example, where the exothermic reaction is a FT process, the reactant substream may comprise fresh syngas and feed from an upstream syngas conversion convention, wherein the feed from the upstream process will comprise a different proportion of inert components.

A means of adjusting the composition of the reactant substream may be provided in at least one of the reaction trains. Preferably, a separate means of adjusting the composition of the reactant substream is provided in each of the reaction trains allowing the composition of the reactant substream to be adjusted independently. The means of adjusting the composition of the reactant substream may comprise introducing recycled reactants into the reactant substream. The proportion of the reactant substream which is made up from recycled reactants may be controlled by adjusting the flow of the recycled reactants into the reactant substream e.g. by the use of a valve, preferably an automated control valve e.g. an automated flow control valve. Alternatively or in addition, the flow rate of the reactant substream prior to addition of the recycled reactants may be adjusted by the use of a valve, preferably an automated control valve e.g. an automated flow control valve. Alternatively, or in addition, the flow rate of the reactant substream subsequent to addition of the recycled reactants (i.e. the combination of the fresh and the recycled reactants) may be adjusted by the use of a valve, preferably an automated control valve e.g. an automated flow control valve. By controlling the flow rate of the recycled reactants and the flow rate of at least one of (i) the reactant substream prior to addition of the recycled reactants and (ii) the reactant substream subsequent to addition of the recycled reactants, it is possible to control the flow rate of the reactants through the reactor thereby ensuring each reaction train meets the desired CO conversion rate or product selectivity.

In one embodiment, the progress of the exothermic reaction in a reactor may be controlled by adjusting the flow rate of the reactant substream through the reaction train of which the reactor forms a part and by adjusting the composition of the reactant substream which is fed into the same reaction train.

In a further embodiment, the progress of the exothermic reaction in at least one reactor is controlled by adjusting the flow rate of the reactant substream through the reaction train of which the at least one reactor forms a part, while the progress of the exothermic reaction in at least one further reactor is controlled by adjusting the composition of the reactant substream through the reaction train of which the at least one further reactor forms a part.

Advantageously, the method of the present invention provides a performance which is at least equivalent to that of current processes. More specifically, where the exothermic reaction is a Fischer-Tropsch process, the conversion of CO from the synthesis gas in the reactant feedstream may be about 70% or higher, preferably about 75% or higher, preferably about 80% or higher, preferably about 85% or higher, preferably about 90% or higher, preferably about 91% or higher, preferably about 92% or higher. In some embodiments, the conversion may be in the range from about 88% to about 95%, alternatively in the range from about 90% to about 94%, alternatively in the range from about 91% to about 93%. The selectivity to methane in the reaction products may be in the range from about 0.01% to about 15%, alternatively about 0.01% to about 10%, alternatively about 1% to about 5%, alternatively from about 3% to about 9%, alternatively from about 4% to about 8%.

Isolating an Individual Reaction Train

As described above, an advantage of the method of the present invention, in particular where the reactant feedstream is divided into at least three reactant substreams, is that it becomes possible to isolate an individual reaction train from the system, while maintaining the remaining reaction trains in an operational state and having minimal impact upon their operation. This is particularly advantageous where the exothermic process involves the use of a heterogeneous catalyst, the performance of which decreases with time such that it will, at some point, require regeneration. It may also prove useful where reloading of the catalyst is required.

In particular, a reaction train may be isolated by (i) providing a second coolant circulation system associated with a second coolant reservoir; (ii) redirecting the coolant to which heat has been transferred from the reaction train to be isolated to the second coolant reservoir; and then (iii) stopping the feed of coolant in step (c) to the reaction train to be isolated while simultaneously initiating the feed of a second coolant from the second coolant reservoir to the reaction train to be isolated.

After step (iii), the operating conditions for the reaction train which has been isolated from the process can be altered to allow for regeneration of the catalyst. Alternatively or in addition, the catalyst may be reloaded while the reaction train is isolated.

When the regeneration (or reloading) of the catalyst has been completed and the isolated reaction train is to be brought back online, it is important to ensure that the steps carried out in isolating the reaction train are performed in reverse. In this regard, an isolated reaction train may be reintroduced by: (iv) reintroducing the coolant stream in step (c) to the isolated reaction train while simultaneously stopping the feed of second coolant from the second reservoir to the isolated reaction train; (v) running the process until the operating conditions of the reactor in the isolated reaction train match those of the reactors which were not isolated; and then (vi) redirecting the coolant to which heat has been transferred from the isolated reaction train to the single common reservoir.

By performing the steps in this order, it is possible to ensure that the isolated reaction train can be brought back online while having minimal impact on the operation of the reaction trains which have remained online throughout the process.

The second coolant may be the same or different from the coolant which is fed to the reaction trains in step (c).

Accordingly, in one aspect, the present invention provides a method of isolating a reaction train from an exothermic reaction process circuit which comprises multiple reaction trains to which a first coolant is fed from a common first coolant reservoir and wherein each reaction train comprises a reactor to which a reactant substream is fed, comprising:
  performing the exothermic reaction in the reactor to produce reaction products and first coolant to which heat has been transferred;
  providing a second coolant circulation system associated with a second coolant reservoir;
  redirecting the first coolant to which heat has been transferred from the reaction train to be isolated to the second coolant reservoir; and then
  stopping the feed of the first coolant to the reaction train to be isolated while simultaneously initiating the feed of the second coolant from the second coolant reservoir to the reaction train to be isolated.

The ability to be able to isolate different reaction trains from the overall process at different times and thus have reaction trains which have different "histories", in particular in relation to the regeneration of the catalyst is unique to the method of the present invention.

In a further aspect, the present invention provides a method of reintroducing a reaction train which has been isolated from an exothermic reaction process circuit which comprises multiple reaction trains to which a first coolant is fed from a common coolant reservoir, wherein each reaction train comprises a reactor to which a reactant substream is fed and wherein:
  an exothermic reaction is performed in the reactor of each reaction train to produce reaction products and first coolant to which heat has been transferred; and
  the isolated reaction train is fed a second coolant from a second coolant reservoir,
the method comprising:
  stopping the feed of the second coolant to the isolated reaction train while simultaneously initiating a feed of first coolant to the isolated reaction train;
  running the process until the operating conditions of the reactor in the isolated reaction train match those of the reactors which were not isolated; and then
  redirecting the first coolant to which heat has been transferred from the isolated reaction train to the common coolant reservoir.

The use of a single common coolant circulation system in conjunction with multiple reaction trains also makes it possible to start up the exothermic process in an efficient and straightforward manner.

Starting Up an Exothermic Reaction

Thus, in one aspect, the present invention provides a method of starting up an exothermic reaction comprising:
  (a) providing at least two separate reaction trains each comprising at least one reactor;
  (b) providing a common coolant circulation system which comprises a single common reservoir comprising a coolant which is fed into each reaction train;
  (c) starting circulation of the coolant to each reaction train;
  (d) increasing the pressure the reactors to a desired reaction pressure;
  (e) feeding a reactant feedstream into each reaction train;
  (f) increasing the temperature of the single common reservoir while adjusting the GHSV of the reactant feedstreams through each reaction train to obtain the desired extent of exothermic reaction.

The first and second coolants may be the same or different.

In an alternative aspect, the present invention provides a method of starting up an exothermic reaction in a start-up reactor comprised in a reaction train, said method comprising
  a) providing multiple reaction trains each comprising at least one reactor;
  b) providing a common coolant circulation system which comprises a single common reservoir comprising a first coolant which is fed into each reaction train except the reaction train comprising the start-up reactor in which the exothermic reaction is to be started up;
  c) providing a second coolant circulation system associated with a second coolant reservoir comprising a second coolant which is fed into the reaction train comprising the start-up reactor;
  d) increasing the pressure in the start-up reactor to a desired reaction pressure;
  e) feeding a reactant feedstream into the reaction train comprising the start-up reactor;
  f) running the process until the operating conditions of the start-up reactor are such that the coolant exiting the start-up reactor may be reintroduced to the common coolant circulation system; and
  g) stopping the feed of the second coolant to the reaction train comprising the start-up reactor while simultaneously initiating a feed of the first coolant to the reaction train comprising the start-up reactor;
  h) redirecting the first coolant from the reaction train comprising the start-up reactor to the single common reservoir.

Some exothermic reactions can initially proceed at a very high rate releasing a large amount of heat. Such exothermic reactions may benefit from being carried out in reactors which are under individual, isolated control during and following start-up of the exothermic reaction. This individual, isolated control may be provided by the use of a second coolant circulation system which is separate from the common coolant circulation system. The use of a method which provides individual, isolated control to the start-up reactor allows isolated control of the start-up reactor operating conditions which may help to prevent thermal runaway during the initial stages of the exothermic reaction.

To avoid losses in production from the exothermic reactions both in the start-up reactor and in the reactors fed by the common coolant circulation system, the method providing the individual, isolated control of the start-up reactor may be maintained until the operating conditions, or the exothermic heat release, of the start-up reactor more closely match those of the reactors which are not in the start-up loop, but are instead fed by the common coolant circulation system. Once this stage has been reached, the start-up reactor can be reintroduced to the common coolant circulation system with minimal impact on production.

When the coolant is a two-phase coolant, the coolant exiting the start-up reactor may be reintroduced to the common coolant circulation system when the operating conditions of the start-up reactor are such that the pressure of the coolant exiting the start-up reactor is not less than the pressure in the common coolant circulation system and, optionally, not more than 100 psi greater than the pressure in the common coolant system.

This isolated start-up method may be carried out on the system shown in FIG. 1 as described below.

As used herein, the term "start-up reactor" is used to describe a reactor during the time in which an exothermic reaction is started or initiated.

The first and second coolants may be the same or different. The type of coolant used may be the same as the coolants listed hereinabove.

The second coolant reservoir may be operated at a temperature in the range from about 25 to about 300° C., from about 100 to about 300° C., or about 200 to about 225° C., or about 200 to about 220° C., or about 205° C. The second coolant reservoir maybe operated at a pressure in the range from about 100 to about 15,000 kPa, or about 100 to about 8600 kPa, or about 450 to about 4100 kPa, or about 450 to about 3400 kPa, or about 1200 to about 2600 kPa, or about 1200 to 2100 kPa, or about 1200 to about 1900 kPa.

In one embodiment, where the coolant is water, the second coolant reservoir may be a second steam drum which is operated at a temperature in the range from 100 to 300° C., in one embodiment (for example where the exothermic reaction is a FT process) 200 to 225° C., or 200 to 220° C., or about 205° C. and a pressure in the range from about 100 to about 8600 kPa, about 100 to about 3400 kPa, in one embodiment, about 1200 to about 2600 kPa, or about 1200 to about 2100 kPa, or about 1200 to about 1900 kPa, or about 1700 to about 1900 kPa.

In this isolated start-up method, the second coolant reservoir may operate at a pressure of from about 180 psia to about 250 psia (about 1240 kPa-about 1725 kPa). This pressure is particularly useful when the exothermic reaction is a Fischer-Tropsch reaction.

The isolated start-up method allows the start-up reactor to be exposed to a temperature ramp to initiate the reaction. The second coolant reservoir is used to provide the temperature ramp over a period of 12 to 24 hours. The temperature ramp may involve increasing the temperature from ambient temperature to between about 170° C. and abut 214° C., e.g. about 205° C. and about 214° C. These temperatures are particularly useful when the exothermic reaction is a Fischer-Tropsch reaction.

Where the coolant is a fluid (e.g. a liquid) which has a boiling point lower than the heat generated by the exothermic reaction, it removes heat from the reaction by undergoing a partial phase change to provide a two phase coolant. During the temperature ramp the temperature and pressure of the two phase coolant as it exits the reactor increases from a starting temperature and pressure to approximately 205° C. and 250 psia. This temperature and pressure increase is often seen when the exothermic reaction is a Fischer-Tropsch reaction.

Controlling the Reactor Temperature

In an alternative embodiment, the single common coolant reservoir method described herein may be provided in a system in which it is possible to individually control the coolant temperature in each reaction train. This embodiment provides all of the advantages associated with the single common coolant reservoir methods described previously, such as the ability to maximize the production capacity of a reaction train in order to exploit economics of scale to minimize unit cost of production. However, in addition, this embodiment allows for the individual temperature control of the individual reactors within the reaction trains.

Accordingly, the present invention provides a method for removing heat from an exothermic reaction comprising:
(a) dividing a reactant feed stream into at least two separate reactant substreams;
(b) feeding each reactant substream into a separate reaction train which comprises a reactor;
(c) feeding a coolant stream from a common coolant reservoir into each reactor;
(d) performing the exothermic reaction in the reactor to produce reaction products and coolant to which heat has been transferred;
(e) feeding the coolant to which heat has been transferred from each reaction train to a single common reservoir in which the heat is removed from the coolant;
(f) feeding the coolant from which the heat has been removed in step (e) back into step (c), wherein:
the coolant is a fluid which has a boiling point lower than the exothermic reaction temperature;
the coolant to which heat has been transferred in steps (d) and (e) is a two phase coolant; and
the progress of the exothermic reaction in each reactor is controlled by adjusting the pressure of the two phase coolant.

Steps (a)-(f) of this embodiment are the same as those previously described and the details provided above for those steps apply equally to this embodiment. This embodiment differs only in its method of controlling the progress of the exothermic reaction in each reactor.

As previously discussed, the reactant substream flows along the reaction train and through the one or more reactors, it is contacted with the catalyst and the exothermic reaction takes place (step (d)). The heat generated by the exothermic reaction is transferred to the coolant, thus removing the heat from the reaction. Hence, step (d) produces reaction products and coolant to which heat has been transferred.

The coolant is a fluid (e.g. a liquid) which has a boiling point lower than the exothermic reaction temperature. It removes heat from the reaction by undergoing a partial phase change to provide a two phase coolant. Consequently, the coolant to which heat has been transferred in steps (d) and (e) is a two phase coolant. Where water is the coolant, steam is generated.

The progress of the exothermic reaction in each reactor may be controlled by adjusting the pressure of the two phase coolant. The pressure of the two phase coolant can be adjusted, which, in turn, adjusts the boiling point of the two phase coolant. This pressure adjustment takes place downstream of the reactor while the two phase coolant is still in the reaction train, i.e. prior to step (e) where the two phase coolant from each reaction train is fed into a single common reservoir. In this way, the pressure can be used to control progress of the exothermic reaction in each reaction train individually. An increase in pressure of the two phase coolant leads to an increase in boiling point of the coolant. This allows the exothermic reaction to be conducted at a higher temperature while maintaining adequate cooling. On the other hand, a decrease in pressure of the two phase coolant leads to a decrease in boiling point of the coolant. Consequently, the exothermic reaction can be conducted at a lower temperature. In this way, the pressure of the two phase coolant can be used to provide the appropriate temperature control for the exothermic reaction.

The pressure of the two phase coolant may be controlled through the use of a valve, e.g. a backpressure two phase flow control or by forward flow control.

In one embodiment, the progress of the exothermic reaction in a reactor may be controlled by adjusting the pressure of the two phase coolant and adjusting the flow rate of the reactant substream through the reaction train of which the reactor forms a part.

In one embodiment, the progress of the exothermic reaction in a reactor may be controlled by adjusting the pressure of the two phase coolant and by adjusting the composition of the reactant substream which is fed into the same reaction train.

In one embodiment, the progress of the exothermic reaction in a reactor may be controlled by adjusting the pressure of the two phase coolant and adjusting the flow rate of the reactant substream through the reaction train of which the reactor forms a part and adjusting the composition of the reactant substream which is fed into the same reaction train.

In one embodiment, the progress of the exothermic reaction in at least one reactor is controlled by adjusting the pressure of the two phase coolant associated with that at least one reactor, while the progress of the exothermic reaction in at least one further reactor may be controlled by adjusting the flow rate of the reactant substream through the reaction train of which the at least one further reactor forms a part.

In one embodiment, the progress of the exothermic reaction in at least one reactor is controlled by adjusting the pressure of the two phase coolant associated with that at least one reactor, while the progress of the exothermic reaction in at least one further reactor may be controlled by adjusting the composition of the reactant substream through the reaction train of which the at least one further reactor forms a part.

In one embodiment, the progress of the exothermic reaction in at least one reactor is controlled by adjusting the pressure of the two phase coolant associated with that at least one reactor, while the progress of the exothermic reaction in at least one further reactor may be controlled by adjusting the flow rate of the reactant substream through the reaction train of which the at least one further reactor forms a part and the progress of the exothermic reaction in at least one still further reactor may be controlled by adjusting the composition of the reactant substream through the reaction train of which the at least one still further reactor forms a part.

This embodiment can also be used in conjunction with the method for isolating an individual reaction train (described above and shown in FIG. 1).

The invention will now be further described by reference to the following figures and examples which are in no way intended to be limiting on the scope of the claims.

Figure 1:
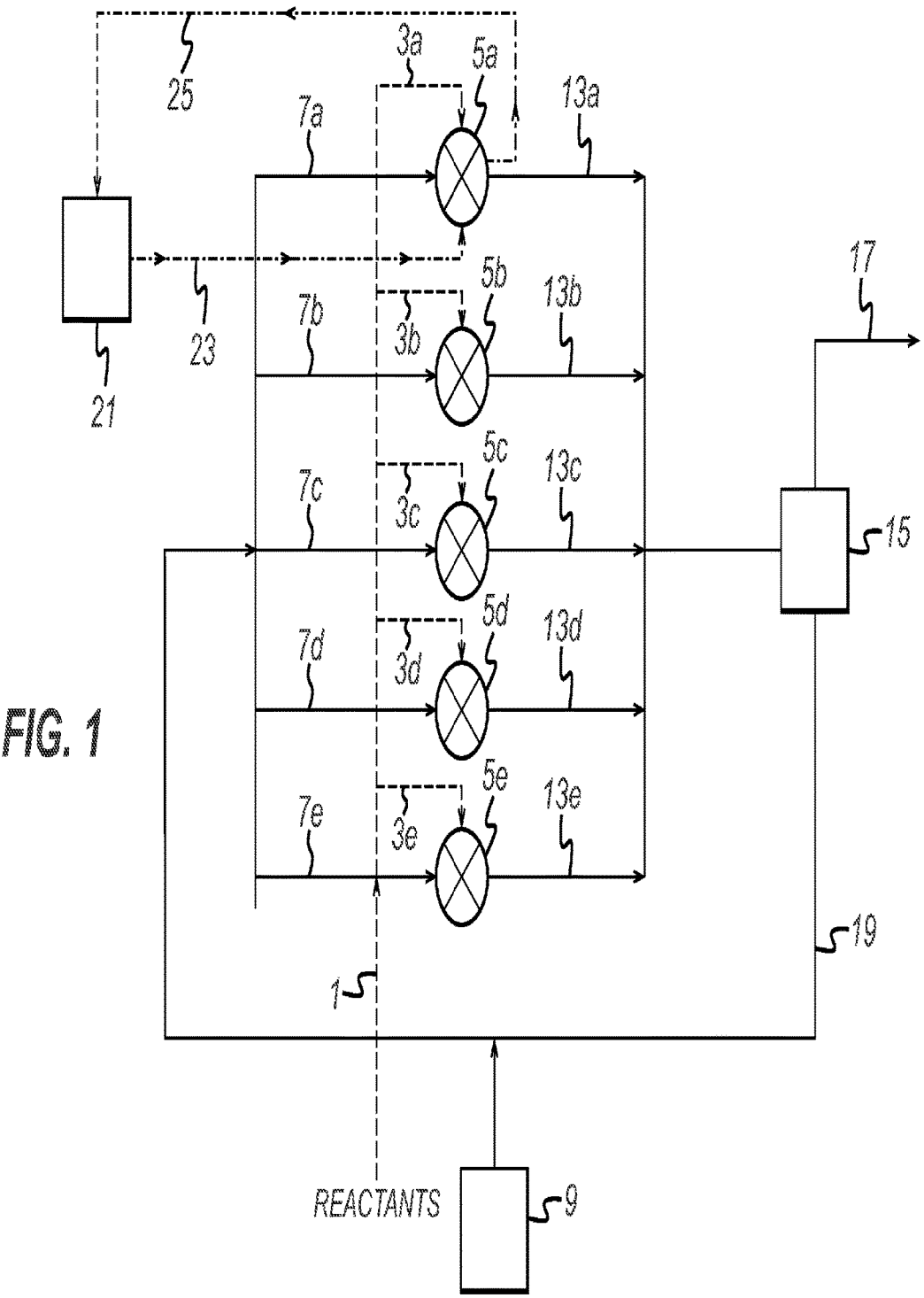
FIG. 1 is a schematic representation of a method for removing heat from an exothermic reaction according to the method of the invention.

In FIG. 1, a reactant feedstream (1) is divided into five reactant substreams which are fed to separate reaction trains (3a, 3b, 3c, 3d, 3e). Each reaction train comprises at least one reactor (5a, 5b, 5c, 5d, 5e) respectively. A coolant stream (7a, 7b, 7c, 7d, 7e) is fed to each reactor from a common coolant reservoir (15). The exothermic reaction is performed in each of the reactors to produce reaction products (11) and coolant to which heat has been transferred (13a, 13b, 13c, 13d, 13e). The coolant to which heat has been transferred is passed to a single common coolant reservoir (15) wherein steam (17) is separated from the coolant stream (19) which is then fed back into the reactors. The figure also shows a second coolant system which comprises a second smaller coolant reservoir (21) from which coolant (23) can be fed and to which coolant to which heat has been transferred can be fed from a reaction train (25).

The method depicted in FIG. 1 can be used to isolate a reaction train or to carry out the isolated start-up method, both described in detail above. The second coolant system shown in FIG. 1 can be used to isolate reaction train 3a or alternatively provide an isolated start-up method in reaction train 3a.

Figure 2:
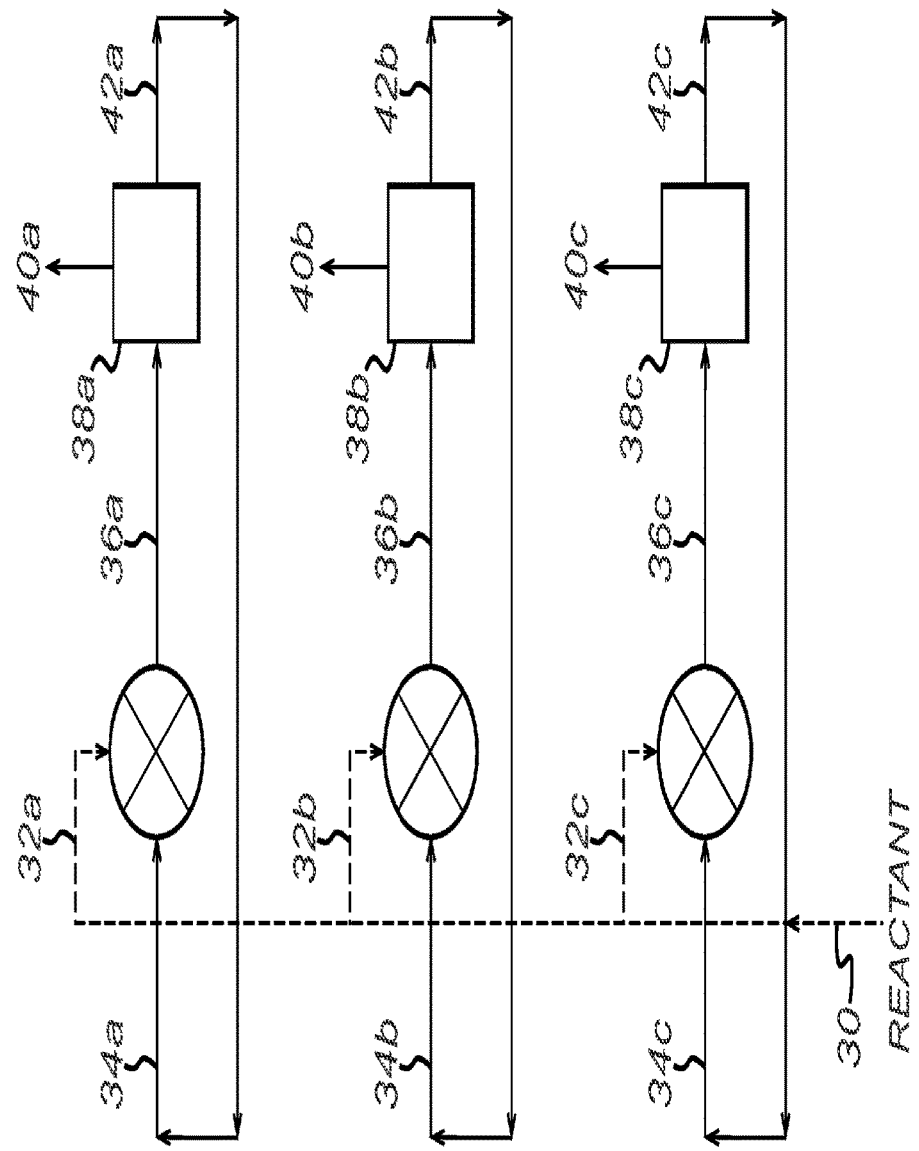
FIG. 2 is a schematic representation of a method for removing heat from an exothermic reaction according to the prior art.

In FIG. 2, a reactant feedstream (30) is divided into three reactant substreams which are fed to separate reaction trains (32a, 32b, 32c). Each reaction train comprises at least one reactor. A coolant stream (34a, 34b, 34c) is fed to each reactor. The exothermic reaction is performed in each of the reactors to produce reaction products and coolant to which heat has been transferred (36a, 36b, 36c). In each reaction train, the coolant to which heat has been transferred is passed to a coolant reservoir (38a, 38b, 38c) wherein steam (40a, 40b, 40c) is separated from the coolant stream (42a, 42b, 42c) which is then fed back into the reactors.

Figure 3:
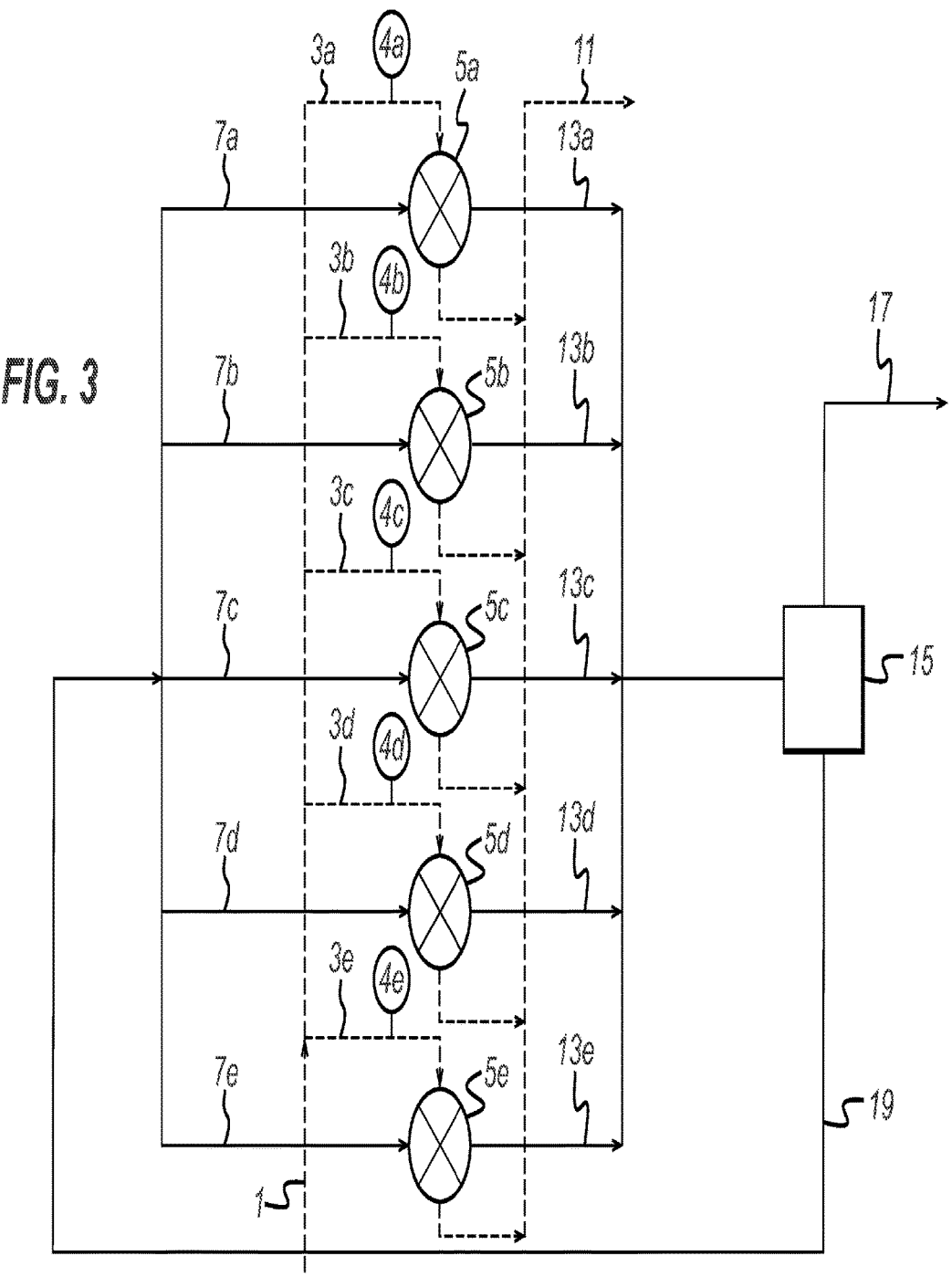
FIG. 3 is a schematic representation of a method for removing heat comprising adjusting the flow rate of the reactant substreams.

In FIG. 3, a reactant feedstream (1) is divided into five reactant substreams which are fed to separate reaction trains (3a, 3b, 3c, 3d, 3e). A means of adjusting the flow rate of each reactant substream is shown (4a, 4b, 4c, 4d, 4e), which may be a valve. Each reaction train comprises at least one reactor (5a, 5b, 5c, 5d, 5e) respectively. A coolant stream (7a, 7b, 7c, 7d, 7e) is fed to each reactor from a common coolant reservoir (15). The exothermic reaction is performed in each of the reactors to produce reaction products (11) and coolant to which heat has been transferred (13a, 13b, 13c, 13d, 13e). The coolant to which heat has been transferred is passed to a single common coolant reservoir (15) wherein steam (17) is separated from the coolant stream (19) which is then fed back into the reactors.

Figure 4:
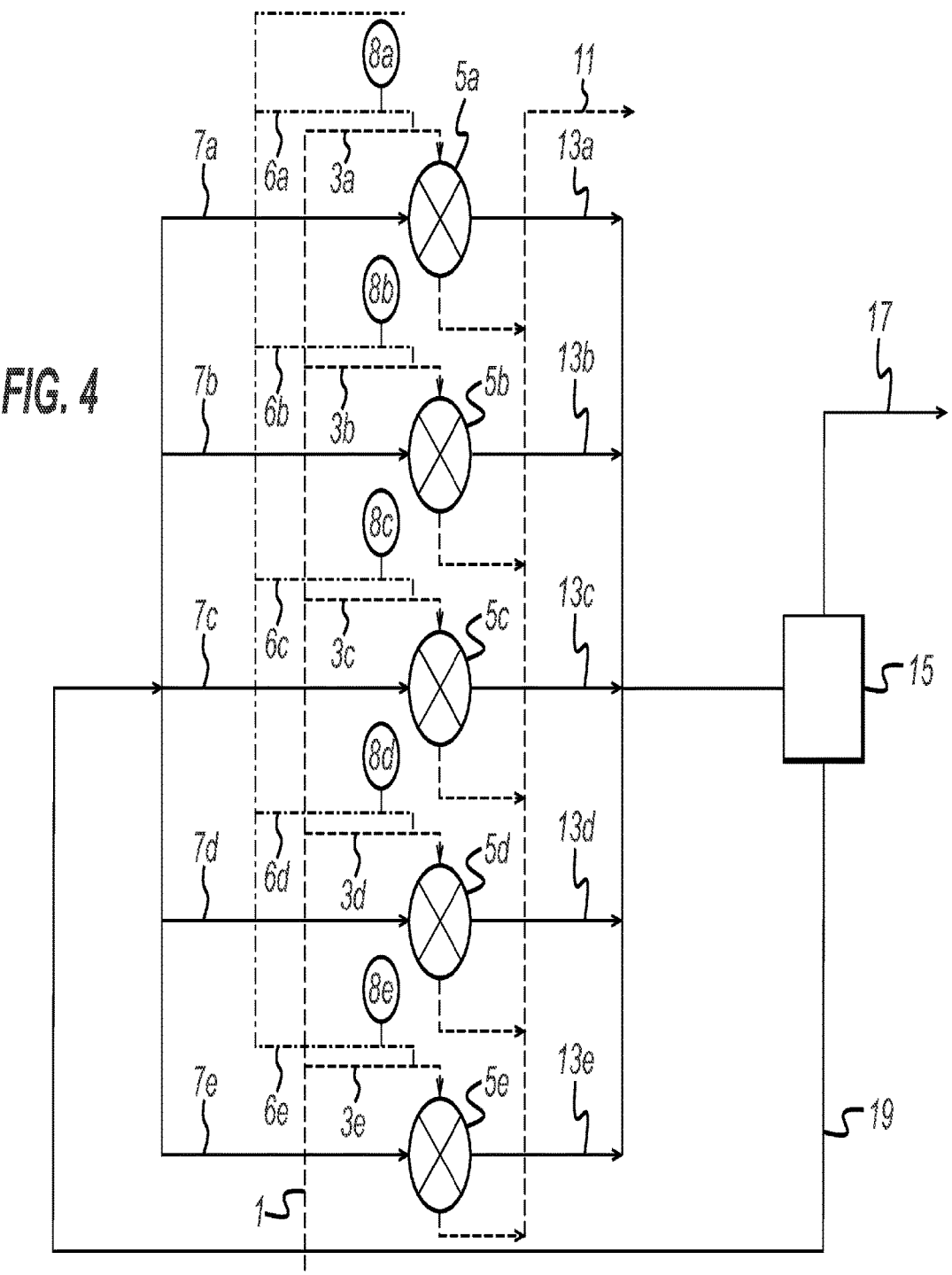
FIG. 4 is a schematic representation of a method for removing heat comprising adjusting the composition of the reactant substreams.

In FIG. 4, a reactant feedstream (1) is divided into five reactant substreams which are fed to separate reaction trains (3a, 3b, 3c, 3d, 3e). A means of adjusting the composition of the reactant substream is shown comprising introducing recycled reactants (6a, 6b, 6c, 6d, 6e) into the reactant substream. The proportion of the reactant substream which is made up from recycled reactants may be controlled by adjusting the flow of the recycled reactants (8a, 8b, 8c, 8d, 8e), e.g. by the use of a valve. Each reaction train comprises at least one reactor (5a, 5b, 5c, 5d, 5e) respectively. A coolant stream (7a, 7b, 7c, 7d, 7e) is fed to each reactor from a common coolant reservoir (15). The exothermic reaction is performed in each of the reactors to produce reaction products (11) and coolant to which heat has been transferred (13a, 13b, 13c, 13d, 13e). The coolant to which heat has been transferred is passed to a single common coolant reservoir (15) wherein steam (17) is separated from the coolant stream (19) which is then fed back into the reactors.

Figure 5:
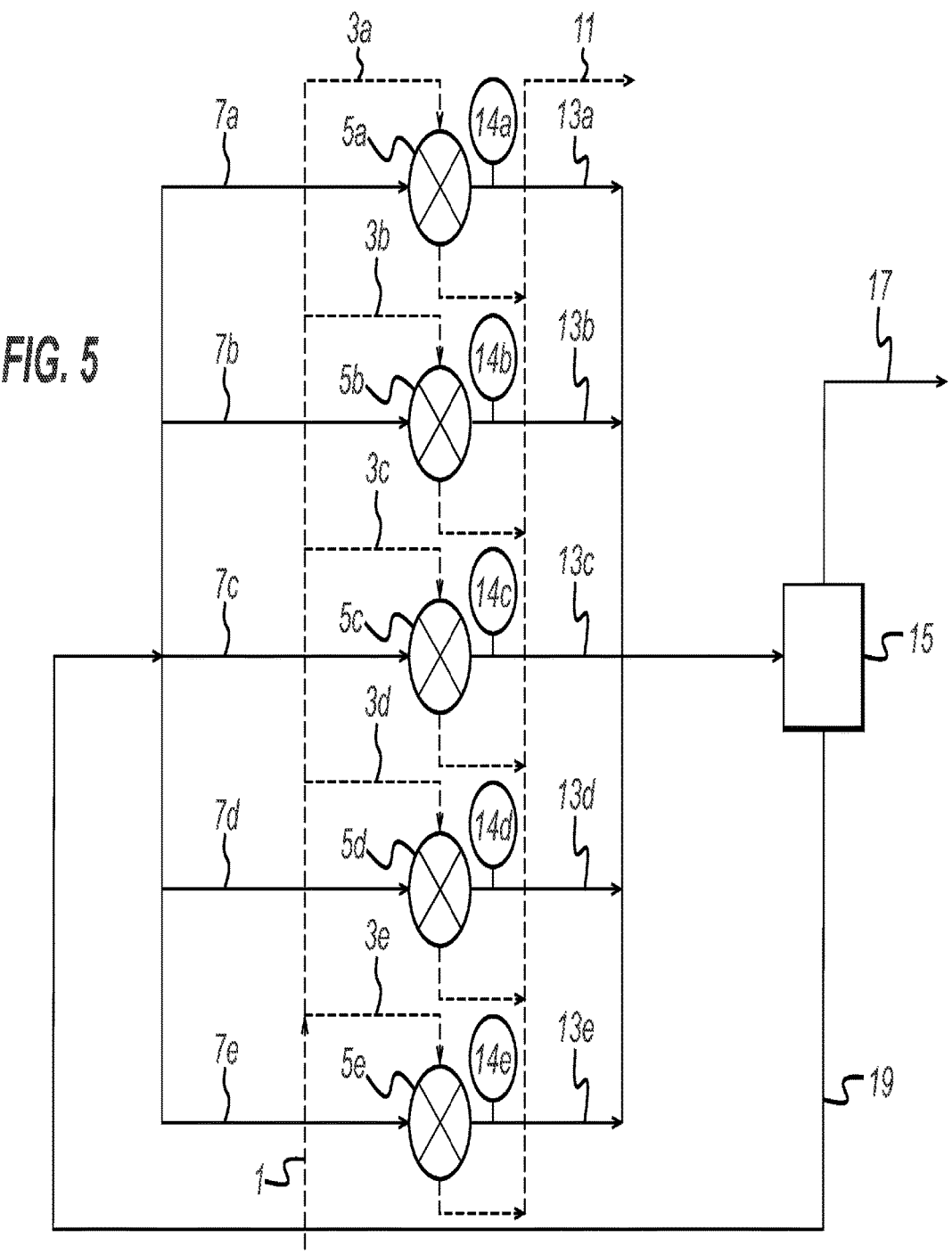
FIG. 5 is a schematic representation of a method for removing heat comprising adjusting the pressure of the two phase coolant.

In FIG. 5, a reactant feedstream (1) is divided into five reactant substreams which are fed to separate reaction trains (3a, 3b, 3c, 3d, 3e). Each reaction train comprises at least one reactor (5a, 5b, 5c, 5d, 5e) respectively. A coolant stream (7a, 7b, 7c, 7d, 7e) is fed to each reactor from a common coolant reservoir (15). The exothermic reaction is performed in each of the reactors to produce reaction products (11) and a two phase coolant to which heat has been transferred (13a, 13b, 13c, 13d, 13e). Means for adjusting the pressure of the two phase coolant is provided (14a, 14b, 14c, 14d, 14e), e.g. valves. The two phase coolant to which heat has been transferred is passed to a single common coolant reservoir (15) wherein steam (17) is separated from the coolant stream (19) which is then fed back into the reactors.

EXAMPLES

Example 1—FT Process

A reactant feedstream (1) comprising synthesis gas (CO and $H_2$) is divided into 5 separate reactant substreams to be fed to five separate reaction trains (3a, 3b, 3c, 3d, 3e). Each reaction train comprises 5 reactors arranged in parallel, each of which contains a fixed-bed of a Fischer-Tropsch catalyst comprising about 40 weight percent cobalt. The ratio of CO to $H_2$ in the reactant feedstream is 0.5. A coolant circulation system comprising water is provided. The circulation is initiated so that water is fed from a single common steam drum (15) to the coolant side of the reactors in each of the separate reaction trains. The water is partially vaporized into a mixture of water and steam, and is then recirculated back to the single common steam drum (15). The temperature and pressure of the single common steam drum is raised to a temperature of 200° C. and a pressure of 14.5 bar(g) at which point the 5 reactant substreams are fed at a flow rate of 15,000 hr$^{-1}$ to their respective reaction trains such that a Fischer Tropsch reaction is initiated in each of the reactors. The synthesis gas reacts in each of the reactors to produce hydrocarbon products and water. The heat generated by the reaction causes the circulating water to partially vapourise such that the coolant leaving the reactor comprises a mixture of water and steam. Once transferred to the single common steam drum, the water and the steam are separated. The steam is removed and the water is recirculated to the reactor trains as described above. Additional water (9) is added to the recycled water to compensate for the removal of the steam. The process is operated at a conversion of 70% $CO_2$. Over time, the activity of the catalyst in each reactor decreases and it is necessary to reduce the GHSV of the reactant feedstream into each reaction train to allow for this and maintain the same level of conversion.

After the activity of the catalyst in reaction train (3a) has decreased to an extent that regeneration was necessary, reaction train (3a) is isolated from the remaining reaction trains in order to separately regenerate the catalyst. This is done by first redirecting the partially vapourised water obtained from the reactors in reaction train (3a) to a second and separate regeneration steam drum (21). The feed of coolant (7a) from the single common steam drum to reaction train (3a) is then stopped at the same time as a feed of water (23) from the second regeneration steam drum (21) is initiated to reaction train (3a). This is done over a period of 30 minutes. The pressure of the steam drum (15) and the pressure of the regeneration steam drum (21) is controlled to the same pressure during the transition to isolate the reaction train (3a). After coolant flow from the regeneration steam drum (21) is established, the regeneration steam drum (21) and the steam drum (15) may be operated independently. Reaction train (3a) is then separated from the remaining reaction trains so that regeneration of the catalyst can be carried out. The pressure of the regeneration steam drum (21) is set to provide the desired temperature set point for coolant flow through the reaction train (3a) during regeneration.

Following regeneration of the catalyst, reaction train (3a) is then brought back online by performing the isolation steps in reverse. More specifically, the coolant feed from the single common steam drum (7a) is reintroduced to the reactors in reaction train (3a) while simultaneously stopping the feed of water to the reactors in reaction train (3a) from the second regeneration steam drum (23). This is done over a period of 30 minutes. The process is then allowed to run until the operating conditions of the reactors in reaction train (3a) match the operating conditions in the remaining reactors. Once this had been achieved, the partially vaporized coolant (13a) obtained from the reactors in reaction train (3a) is redirected to the single common steam drum (15).

An analogous process is repeated when the catalyst in the other reaction trains required regeneration.

Example 2—Methanol Production

A reactant feedstream (1) comprising synthesis gas (CO and $H_2$) is divided into 5 separate reactant substreams to be fed to five separate reaction trains (3a, 3b, 3c, 3d, 3e) (see FIG. 3). Each reaction train comprises 1 microchannel reactor, each of which contains a fixed-bed of a Cu/ZnO/$Al_2O_3$ catalyst. The reactant feedstream contained 5 mol % $CO_2$, 26 mol % CO, 64 mol % $H_2$ and 5 mol % $N_2$. The reactant feedstream is fed to the reactor at 250° C. and 50 bar(g) at 1,500 hr$^{-1}$. A coolant circulation system comprising water is provided. The circulation is initiated so that water is fed from a single common steam drum (15) to the coolant side of the reactors in each of the separate reaction trains. In the reactors, the water is partially vaporized into a mixture of water and steam, and is then recirculated back to the single common steam drum (15). The temperature and pressure of the single common steam drum is raised to a temperature of 250° C. and a pressure of 39 bar(g). Once in the reaction train, the flow rate of each reactant substream may be adjusted individually using automated flow control valves (4a, 4b, 4c, 4d, 4e) to account for factors such as the deactivation of the catalyst in the reactor present in that reaction train.

The synthesis gas reacts in each of the reactors to produce methanol. The heat generated by the reaction causes the circulating water to partially vaporize such that the coolant leaving the reactor comprises a mixture of water and steam. Once transferred to the single common steam drum, the water and the steam are separated. The steam is removed and the water is recirculated to the reactor trains as described above. Additional water is added to the recycled water to compensate for the removal of the steam.

Example 3—Isolated Start-Up Method

A reactant feedstream (1) comprising synthesis gas (CO and $H_2$) is divided into 4 separate reactant substreams to be fed to four separate reaction trains (3b, 3c, 3d, 3e) (see FIG. 1). Each reaction train comprises one reactor containing a fixed-bed of a Fischer-Tropsch catalyst comprising about 40 weight percent cobalt. The ratio of CO to $H_2$ in the reactant feedstream is typically from 0.5 to 0.6. A common coolant circulation system comprising water is provided. During circulation, water is fed from a single common steam drum (15) to the coolant side of the reactors in each of the separate reaction trains. The water is partially vaporized into a mixture of water and steam, and is then recirculated back to the single common steam drum (15). The single common steam drum operates at a temperature of about 205° C. and the coolant temperature at the reactor exit may be between 205° C. and 214° C. The single common steam drum provides a maximum pressure of 19.7 bar(g) (300 psia or 2068 kPa) at the reactor coolant exit. The 4 reactant substreams are fed at a flow rate of between 12,000 $hr^{-1}$ and 15,000 $hr^{-1}$ to their respective reaction trains such that a Fischer-Tropsch reaction is operated at a similar CO conversion in each of the reactors. The synthesis gas reacts in each of the reactors to produce hydrocarbon products and water. The heat generated by the reaction causes the circulating water to partially vaporize such that the coolant leaving the reactor comprises a mixture of water and steam. Once transferred to the single common steam drum, the water and the steam are separated. The steam is removed and the water is recirculated to the reactor trains as described above. Additional water (9) is added to the recycled water to compensate for the removal of the steam. The water may optionally be heated between the steam drum and the reactors. The process is operated at a CO conversion in a narrow range, typically from 68% to 72%.

Regulation of the pressure differential between the reactor coolant exit and the common steam drum (15) is achieved through the use of restriction orifices. Between one and five silicon carbide restriction orifices are positioned on the coolant outlet between the reactor exit (13b, 13c, 13d, 13e) and the common steam drum (15) allowing a pressure change in steps up of 10 psi as the flow path is lined up to a selected orifice or selected orifices thereby regulating the pressure differential of the coolant between each reactor and the common steam drum. Water may optionally be heated to a desired temperature in the range from 205 to 214° C. between the steam drum exit and the coolant inlet to the reactor.

Reaction train (3a) comprises start-up reactor (5a) in which an exothermic Fischer-Tropsch reaction is to be started up. Reaction train (3a) is fed by a second coolant circulation system, also using water as a coolant and associated with second steam drum (21). The Fischer Tropsch reaction is initiated in start-up reactor (5a) by increasing the pressure of the start-up reactor steam drum to 250 psia and starting the reactant substream in reaction train (3a). The second coolant circulation system is used to increase the start-up reactor (5a) temperature from ambient temperature to 205° C. over a time of 12 to 24 hours. During this time, the two phase coolant as it exits the reactor increases from a starting temperature and pressure to 250 psia and 205° C.

When the operating conditions of reactor (5a) are such that the coolant outlet pressure is sufficiently high enough, the coolant exiting reactor (5a) may be reintroduced to the common steam drum and coolant from the common coolant circulation system is introduced into reactor (5a). The coolant feed from the single common steam drum (7a) is thus reintroduced to the reactor in reaction train (3a) while simultaneously stopping the feed of water to the reactors in reaction train (3a) from the second steam drum (23). Once this had been achieved, the partially vaporized coolant (13a) obtained from the reactors in reaction train (3a) is redirected to the single common steam drum (15).

The invention claimed is:

1. A method of isolating a reaction train from an exothermic reaction process circuit which comprises multiple reaction trains to which a first coolant is fed from a common first coolant reservoir and wherein each reaction train comprises a reactor to which a reactant substream is fed, comprising:
performing the exothermic reaction in the reactor to produce reaction products and first coolant to which heat has been transferred;
providing a second coolant circulation system associated with a second coolant reservoir;
redirecting the first coolant to which heat has been transferred from the reaction train to be isolated to the second coolant reservoir; and then
stopping the feed of the first coolant to the reaction train to be isolated while simultaneously initiating the feed of the second coolant from the second coolant reservoir to the reaction train to be isolated.

2. The method according to claim 1, wherein the first coolant and the second coolant are the same.

3. The method according to claim 1, wherein the first coolant and the second coolant are different.

4. A method of reintroducing a reaction train which has been isolated from an exothermic reaction process circuit which comprises multiple reaction trains to which a first coolant is fed from a common coolant reservoir, wherein each reaction train comprises a reactor to which a reactant substream is fed and wherein:
an exothermic reaction is performed in the reactor of each reaction train to produce reaction products and first coolant to which heat has been transferred; and
the isolated reaction train is fed a second coolant from a second coolant reservoir,
the method comprising:
stopping the feed of the second coolant to the isolated reaction train while simultaneously initiating a feed of first coolant to the isolated reaction train;
running the process until the operating conditions of the reactor in the isolated reaction train match said reactors which were not isolated; and then
redirecting the first coolant to which heat has been transferred from the isolated reaction train to the common coolant reservoir.

5. The method according to claim 1, wherein the exothermic reaction is selected from the group consisting of a Fischer-Tropsch reaction, methanol production and ethylene oxide production.

6. The method according to claim 1, wherein the exothermic reaction is a Fischer-Tropsch reaction.

7. The method according to claim 1, wherein the exothermic reaction involves the use of a heterogeneous catalyst.

8. The method according to claim 7, wherein after the step of stopping the feed of the first coolant, the operating conditions for the reactant train which has been isolated from the process are altered to allow for regeneration of the catalyst.

9. The method according to claim 7, wherein the catalyst is reloaded while the reaction train is isolated.

10. The method according to claim 7, wherein the first coolant is water.

11. The method according to claim 7, wherein the catalyst has been regenerated and the isolated reaction train is brought back online by: reintroducing the feed of the first coolant to the isolated reaction train while simultaneously stopping the feed of the second coolant from the second reservoir to the isolated reaction train; then running the process until the operating conditions of the reactor in the isolated reaction train match those of the reactors which were not isolated; and then redirecting the coolant to which heat has been transferred from the isolated reaction train to the common coolant reservoir.

* * * * *